United States Patent
Blum et al.

(10) Patent No.: US 9,668,742 B2
(45) Date of Patent: Jun. 6, 2017

(54) OCCLUSION DEVICE

(71) Applicant: Cook Medical Technologies LLC, Bloomington, IN (US)

(72) Inventors: Kevin Blum, West Lafayette, IN (US); Sara M. Sherman, Lafayette, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 154 days.

(21) Appl. No.: 14/645,563

(22) Filed: Mar. 12, 2015

(65) Prior Publication Data

US 2015/0257763 A1    Sep. 17, 2015

Related U.S. Application Data

(60) Provisional application No. 61/951,777, filed on Mar. 12, 2014.

(51) Int. Cl.
*A61B 17/12* (2006.01)
*A61B 17/00* (2006.01)

(52) U.S. Cl.
CPC .. *A61B 17/12109* (2013.01); *A61B 17/12177* (2013.01); *A61B 2017/00526* (2013.01); *A61B 2017/00597* (2013.01); *A61B 2017/00606* (2013.01); *A61B 2017/00893* (2013.01)

(58) Field of Classification Search
CPC ........ A61B 17/12109; A61B 17/12113; A61B 17/12099; A61B 17/12027; A61B 17/12022; A61B 17/12031; A61B 17/12036; A61B 17/1204; A61B 17/12168; A61B 17/12177; A61B 2017/00893; A61B 2017/00597; A61B 2017/00606; A61B 2017/00526; A61L 27/507

See application file for complete search history.

(56) References Cited

U.S. PATENT DOCUMENTS

| | | | |
|---|---|---|---|
| 6,265,333 | B1 | 7/2001 | Dzenis et al. |
| 7,413,575 | B2 | 8/2008 | Phaneuf et al. |
| 8,262,979 | B2 | 9/2012 | Anneaux et al. |
| 8,346,339 | B2 | 1/2013 | Kordis et al. |
| 2003/0100944 | A1 | 5/2003 | Laksin et al. |
| 2005/0113868 | A1 | 5/2005 | Devellian et al. |

(Continued)

FOREIGN PATENT DOCUMENTS

WO    2013/028387 A2    2/2013

*Primary Examiner* — Jocelin Tanner
(74) *Attorney, Agent, or Firm* — Brinks Gilson & Lione

(57) ABSTRACT

An occlusion device for placement within a body vessel may include a wire constructed support structure having a covering applied thereto. The covering includes a mixture of PET and ultra-high molecular weight polyethylene (UHMWPE). The covering is applied to the support structure via an electrospinning process to produce a non-woven fiber covering having increase strain capabilities relative to an electrospun PET covering without UHMWPE. The device has a nominal state that is radially expanded and a delivery state that is radially compressed and longitudinally extended for disposal within a low-profile delivery sheath. The covering increased strain capability allows for the device to have relative large diameter in the nominal state while still being capable of low-profile delivery. This occlusion device can provide faster occlusive capability when deployed and does not rely on delayed embolization. The covering extends across the vessel upon deployment to provide instant occlusion.

20 Claims, 4 Drawing Sheets

(56) References Cited

U.S. PATENT DOCUMENTS

| | | |
|---|---|---|
| 2007/0087027 A1 | 4/2007 | Greenhalgh et al. |
| 2008/0027531 A1 | 1/2008 | Reneker et al. |
| 2008/0033522 A1 | 2/2008 | Grewe et al. |
| 2008/0200975 A1 | 8/2008 | Dubson |
| 2008/0217241 A1 | 9/2008 | Smithies et al. |
| 2011/0236744 A1 | 9/2011 | Kim et al. |
| 2011/0301630 A1 | 12/2011 | Hendriksen et al. |
| 2012/0035706 A1 | 2/2012 | Paul, Jr. et al. |
| 2012/0184609 A1 | 7/2012 | Jamison et al. |
| 2012/0259170 A1 | 10/2012 | Grewe et al. |
| 2013/0150963 A1 | 6/2013 | Johnson |

OCCLUSION DEVICE

CROSS REFERENCE TO RELATED APPLICATIONS

This application claims the benefit of U.S. Provisional Patent Application No. 61/951,777, filed on Mar. 12, 2014, the entire contents of which is hereby incorporated by reference.

TECHNICAL FIELD

This disclosure relates to endoluminal medical devices for implantation within the human or animal body for treatment of endovascular disease. More particularly, it relates to an endoluminal occlusion device having a covering material and methods of manufacturing such an endoluminal occlusion device.

BACKGROUND

Peripheral occlusion is used clinically for a wide variety of vascular pathologies. One type of device is a vascular plug, which has been used to treat pulmonary arteriovenous malformations, anomalous venous connections, and internal iliac artery aneurysm with or without abdominal aortic aneurysm. Typical vascular occlusion devices or plugs can generally occlude blood flow through a branching vessel or other vessel.

One type of plug is in the form of an expandable mesh that can expand to fill a hole or gap in the heart or blood vessel. These plugs expand and over time blood will clot on the mesh and eventually block blood from travelling into or through the hole.

Another type of plug is in the form of a coil. The coil will wind into a predetermined shape within a blood vessel after deployment. Over time, blood will clot on and around the coil to eventually block blood flow into or through the vessel.

However, improvements can be made. For example, these typical vascular occlusion devices do not immediately occlude blood flow through the vessel. Rather, they require time for blood to clot on the device.

Another type of implantable medical device is in the form of a covered stent that can be used to treat peripheral disease. These covered stents include a support frame or stent that includes a graft material attached thereto. These stent-grafts are typically used to ensure that blood will continue to flow through a diseased vessel, with the stent expanding into contact with the vessel wall. The stent-graft includes a lumen therethrough that permits blood to flow. However, these devices will not occlude or prevent flow.

These stents or stent-grafts can include coverings that are typically applied when the support frame is in an expanded condition, and the stent-graft is then compressed for delivery. This compression is radially applied, and when released, the stent-graft will expand into engagement with the target blood vessel.

However, these typical covering materials are not resistance to relatively high strain, limited the amount that they can be stretched relative to their initial state. This covering material can be radially compressed and folded over itself, but this limits the amount that the devices can be compressed for delivery.

Thus, improvements can be made to covering materials that are applied to medical device support structures.

SUMMARY

The present embodiments provide an occlusion device having a support structure covered by a mixture of electrospun PET and ultra-high molecular weight polyethylene (UHMWPE) and methods of manufacturing such an occlusion device.

In one example, a medical device for placement within a body vessel for providing vessel occlusion is provided. The device includes a support structure having proximal and distal ends and defining a longitudinal axis therebetween, wherein the support structure is biased toward a nominal state having a radial expanded and longitudinally shortened configuration and extendable from the nominal position to a lengthened state having a radially reduced and longitudinally lengthened configuration. The device includes at least one layer of nonwoven electrospun fibers attached to and encapsulating the support structure. The electrospun fibers comprise a mixture of Polyethylene Terephthalate (PET) solution and Ultra High Molecular Weight Polyethylene (UHMWPE) micro-particles.

A method for coating a support structure with a non-woven electrospun material is provided. The method includes the steps of: attaching a support structure to a conductive mandrel; rotating the mandrel; applying a mixture of ultra high molecular weight polyethylene (UHMWPE) microparticles and Polyethylene Terephthalate (PET) solution to the support structure by electrospinning; and coating the support structure with non-woven electrospun fibers produced by electrospinning the mixture to produce at least one layer of non-woven electrospun fibers.

BRIEF DESCRIPTIONS OF THE DRAWINGS

DETAILED DESCRIPTION OF THE DRAWINGS AND THE PRESENTLY PREFERRED EMBODIMENTS

The present disclosure relates to an endoluminal occlusion device having a covering material and methods of manufacturing such an endoluminal occlusion device.

In the present disclosure, the term "proximal" refers to a direction that is generally closest to the heart during a medical procedure, while the term "distal" refers to a direction that is farthest from the heart during a medical procedure.

Figure 1:
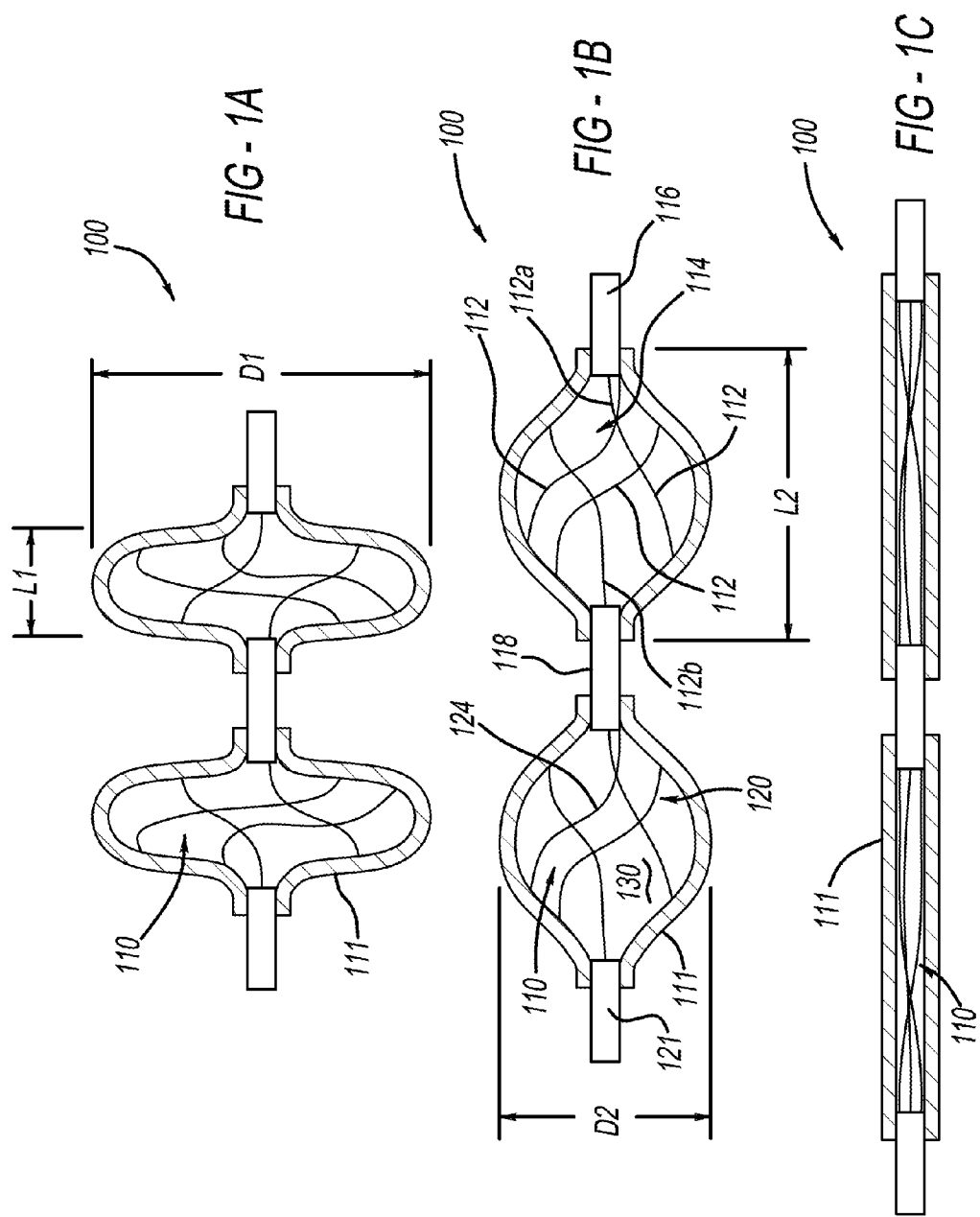
FIG. 1A illustrates one example of an occlusion device in a nominal state.
FIG. 1B illustrates the occlusion device of FIG. 1A in an intermediate state.
FIG. 1C illustrates the occlusion device of FIG. 1A in a lengthened state.

FIG. 1 illustrates one example of an endoluminal occlusion device 100. In this example, the device 100 is a covered occlusion device or vascular plug. The device 100 may include a support structure 110 and a covering 111 attached to the support structure. In one example, the support structure 110 may be encapsulated within the covering 111 as shown in FIG. 1 and further described below. Of course, it will be appreciated that the support structure 110 could be partially encapsulated in some forms. The support structure may 110 have any configuration known in the art that is suitable for generally immediate expansion across a vessel. The support structure may be configured as a unitary structure or a plurality of separate structures which may collectively define the support structure. Additionally, or alternatively, the support structure may be in the form of a woven wire structure or another pattern or design.

The support structure 110 may add rigidity, expansion force, and/or support to the prosthesis 100. To that end, the support structure 110 may be made from one or more of numerous metals and/or alloys. For example, the support structure 110 may be made from a metallic material such as stainless steel, silver, platinum, palladium, gold, titanium, tantalum, iridium, tungsten, cobalt, chromium, cobalt-chromium alloy 1058, cobalt-based 35N alloy, nickel-based alloy 625, a molybdenum alloy, such as a molybdenum alloy including about 0.4% to about 0.8% of lanthanum oxide ($La_2O_3$), and a nickel-titanium alloy, such as nitinol, or other suitable materials known in the art. In one example, the support structure 110 may include a shape-memory or superelastic material such as nitinol. The chosen material will preferably allow the support structure to have a nominal state from which it can be stretched or compressed in response to an external force and will return toward its nominal state when the external force is reduced or removed.

The covering 111 may be attached to the support structure 110, which will be further described below. The covering can be applied to both the external and internal surfaces of the support structure to encapsulate the support structure. Preferably, once applied, the covering 111 will prevent fluid flow through the support structure 110, such that when the structure 110 spans across a body vessel or other lumen, flow through the vessel or the lumen would be prevented.

In one example, the support structure 110 may include a plurality of interconnected wires 112 that combine to form a mesh 114. The wires 112 can each have proximal ends 112a and distal ends 112b. The proximal ends 112a are connected at a first hub 116 and the distal ends are connected at a second hub 118. The first and second hubs 116, 118 can be defined by the proximal and distal ends 112a, 112b, respectively where the ends of the wires 112 are bunched and held together in a manner known in the art, such as through adhesive, bonding, welding, mechanical connection, or the like. Additionally, or alternatively, the hubs 116 and 118 can be in the form of a distinct component, such as a tube, sleeve, cylinder, or the like that can be attached to the ends 112a or 112b in a manner known in the art.

The mesh 114 is configured to have both a nominal state and a lengthened state, as well as intermediate states therebetween. In the nominal state, shown in FIG. 1A, the mesh 114 will have a generally circular or flattened disc-shape having a first diameter D1 that is sized and configured to be greater than the diameter of the target vessel. Accordingly, the mesh 114 will have a first length L1 that is relatively short. The mesh 114 is biased toward this nominal state, such that when freed from external forces or restriction, the mesh 114 will return toward this short length and wide diameter.

In an intermediate state, shown in FIG. 1B, the mesh 114 will have a second diameter D2 that is smaller than the first diameter, a length L2 that is longer than the first length L1 and have a rounder shape.

In the lengthened state, shown in FIG. 1C, the mesh 114 will have a third diameter D3 that is smaller than the first diameter D1 and second diameter D2 and have an elongate shape. The mesh 114 will also have a third length L3 that is longer the first length L1 and the second length L2.

Typically, as the mesh 114 is lengthened, the diameter decreases. As the mesh 114 is shortened, the diameter increases. Thus as the mesh 114 is allowed to expand radially back toward its nominal state, the length of the mesh 114 will decrease.

The wire 112 forming the mesh 114 are preferable arranged in a criss-cross pattern to define the mesh 114; however, other arrangements of the wires can also be used to create a radial support structure in the nominal state. When the mesh 114 is in its lengthened state, the wires 112 will approach a generally parallel configuration having a low radial profile as shown in FIG. 1C. This low profile reduces the overall diameter of the device in the lengthened state, allowing for a reduced diameter delivery configuration. Accordingly, the lengthened state can also be referred to as a delivery configuration. The device 100 also has a deployed configuration, where the diameter of the device is increased, such as the states shown in FIGS. 1A and 1B, so as to contact the vessel wall after deployment. However, it will be appreciated that the diameter in the deployed configuration can be smaller than the nominal diameter, such as that shown in FIG. 1B, with the bias of the device 110 toward the nominal state shown in FIG. 1A acting against the vessel walls to retain the device in the vessel.

The device 110 can include more than one mesh 114. In one form, the device includes a second mesh 120. The second mesh 120 is aligned longitudinally with the mesh 114. When more than one mesh is used, the second hub 118 can be referred to as an intermediate hub that connects the first mesh 114 and the second mesh 120. When more than one mesh is used, a third hub 121 can be used to join the ends of the second mesh 120 opposite the second hub 118. It will be appreciated by those skilled in the art that additional meshes, such as a third, fourth, fifth, etc. mesh can be used. Each additional mesh can include additional hubs.

The second mesh 120 can be constructed in a similar manner to the first mesh 114. For example, the second mesh 120 can also include a plurality of wires 124 and can be sized and configured to move from a longitudinally short and radially expanded nominal state to a longitudinally extended and radially compressed lengthened state. The second mesh 120 can be sized such that the radial expansion in the nominal state of the second mesh 120 corresponds to the radial expansion of the first mesh 114.

In another approach, the second mesh 120 can be sized and configured to expand to a greater radial size when in the nominal state relative to the first mesh 114. In this approach, the plurality of wires 124 of the second mesh 120 will be generally longer than the plurality of the wires 112 of the first mesh 114. The relatively longer length will allow the second mesh 120 to expand to the larger diameter due to the added length. Accordingly, the second mesh 120 will extend to a longer length in the lengthened state.

In another approach, the second mesh 120 can be sized and configured to expand to a smaller radial size when in the nominal state relative to the first mesh 114. In this approach, the plurality of wires 124 of the second mesh 120 will be generally shorter than the plurality of the wires 112 of the first mesh 114. The relatively shorter length will allow the second mesh 120 to expand to the smaller diameter due to the reduced length. Accordingly, the second mesh 120 will extend to a shorter length in the lengthened state. However, in another aspect, the length of the wires 124 of the second mesh 120 could be same length while being arranged to expand to a smaller radial size by altering the heat setting characteristics. Superelastic materials can be given any nominal diameter within material characteristics based on heat setting.

Of course, the second mesh 120 could also be constructed in another manner to alter its radial size relative to the first mesh 114.

The above discussion regarding the first and second meshes 114, 120 refers to the meshes 114, 120 being moveable from a radial expanded nominal state to a longitudinally extended lengthened state. As described previously, the lengthened state is preferably used for delivering the device 100 to target vessel for delivery and deployment of the device within the vessel to quickly occlude blood flow. The ability to substantially lengthen the mesh 114 allows for the device 100 to be delivered through narrow and tortuous body vessels, and subsequently be able to radially expand to block relatively large body vessels.

As described above, the support structure 110 of the device 100 includes the covering 111. The covering 111 is used, once delivered and deployed, to quickly occlude blood flow through the vessel in which it is deployed. This is due to the generally blood-impermeable nature of the covering material. With the device 100 radially expanded to its nominal state, the support structure 110 and covering 111 will span the width of the vessel, thereby preventing blood flow generally immediately, in contrast to coil type occlusion devices or the like that require blood to clot over time to form an occlusive barrier.

As further described below, the covering 111 is configured to expand both radially and longitudinally. The covering 111 is able to withstand relatively large strain applied thereto when the covering is longitudinally extended in the lengthened state. This beneficial extension capability is due to the combination of the material used and the manner of applying the covering 112 to the support structure 110. The covering 112 is applied to the support structure 110 by electrospinning, which is described in further detail below.

The covering 111, when applied to the support structure 110 to encapsulate the support structure 110, can thereby define a cavity 130 therein, where the cavity 130 will expand and contract in accordance with the expansion and extension of the support structure 110.

The above description of the support structure 110 has referred to a wire based structure that can radially expand to block blood flow when covered, and can longitudinally extend to reduce the radial profile for delivery while having a covering that can withstand relatively high strain levels. It will be appreciated that other support structure types can also be used with this high strain resistant covering, such as traditional tubular shaped stent-graft designs, such as those disclosed in U.S. patent application Ser. No. 13/618,356, filed Sep. 14, 2012, which is hereby incorporated by reference in its entirety.

The covering 111 may be formed of any suitable biocompatible covering or graft material. In one example, the material may be deposited onto the support structure 110 using an electrospinning process as further described below. Many different types of biocompatible materials may be used to form the covering 111. The biocompatible material may be substantially non-toxic in the in vivo environment of its intended use, and may be substantially unrejected by the patient's physiological system (i.e., may be non-antigenic). In one approach, the biocompatible material preferred for use with the device 100 is a combination of Polyethylene Terepthlate (PET) and ultra-high molecular weight polyethylene (UHMWPE). This material is preferably in the form of a solution that is applied to the support structure 110 via electrospinning, further described below.

Although the discussion in this disclosure will refer to the occlusion device 100, a person having ordinary skill in the art will recognize that the devices and methods described herein may be equally applicable to an occlusion device or prosthesis, such as a stent or stent graft, having other configurations. Such devices and methods are contemplated by and within the scope of this disclosure.

Figure 2:
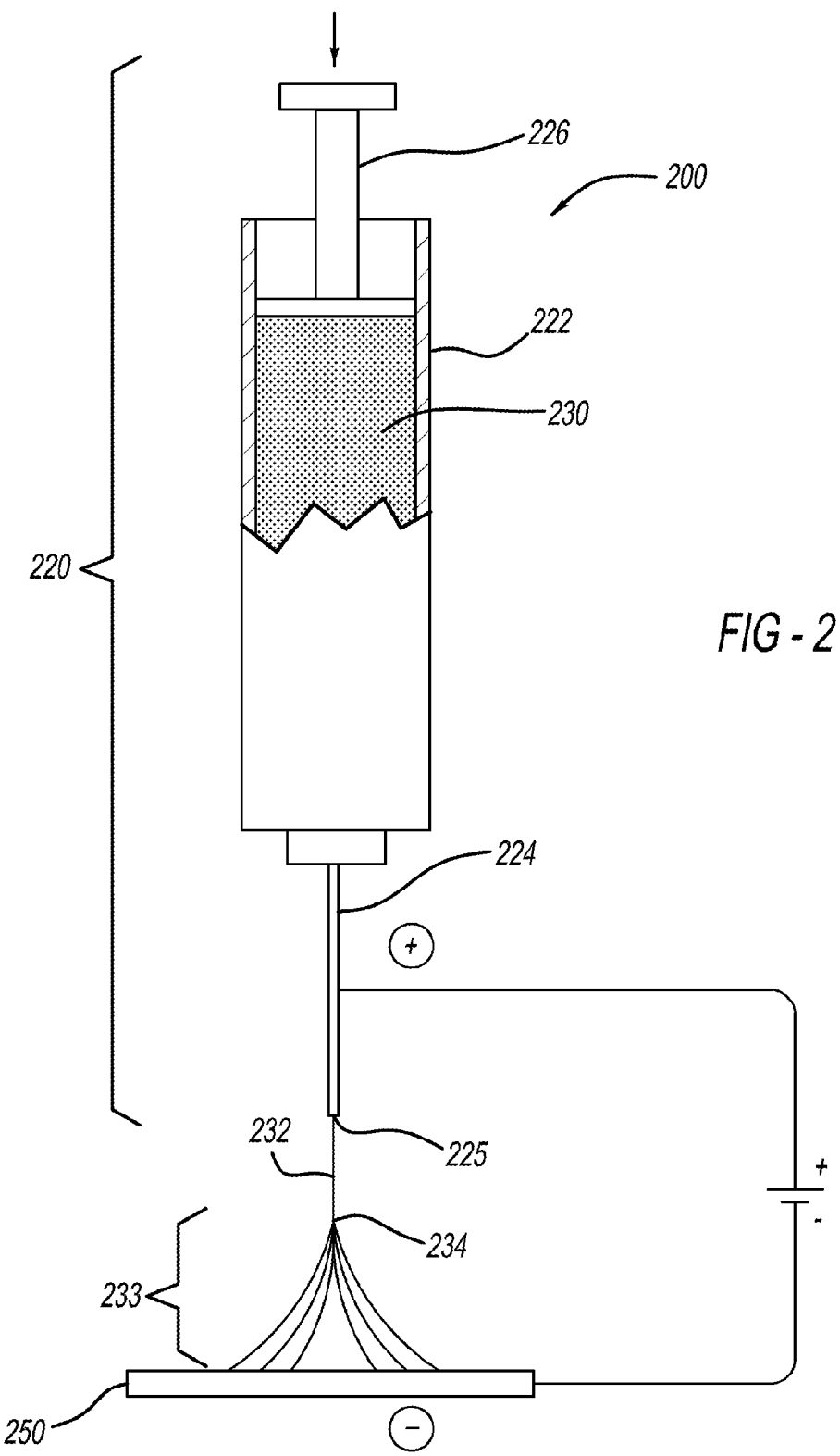
FIG. 2 illustrates one example of an electrospinning apparatus.

FIG. 2 illustrates one example of an electrospinning apparatus 200 for coating an object, such as a substrate or a medical device. The electrospinning apparatus 200 may be similar to that described in U.S. Pat. No. 7,799,261 to Orr et al., which is incorporated herein by reference. For example, the electrospinning apparatus 200 may include a spinneret 220. The spinneret 220 may include a reservoir 222, which may be configured as a syringe-like container as shown in FIG. 2. The reservoir 222 may be fluidly coupled to an orifice 224 to form the spinneret 220. The orifice 224 may be configured as a needle as shown in FIG. 2.

A solution 230 may be loaded into the reservoir 222. More particularly, the solution of PET and UHMWPE may be loaded into the reservoir. The solution 230 will be discussed in more detail below. The orifice 224 may have a distal opening 225 through which the solution 230 may be driven by a displacement system 226. The displacement system 226 may be configured as any type of controllable, variable rate fluid displacement system. For example, the fluid displacement system 226 may be configured as a plunger as shown in FIG. 2. Preferably, the displacement system 226 may be an automated system to provide a consistent and accurate flow of solution 230 through the orifice 224. In one example, the fluid displacement system 226 may deliver the solution 230 at a delivery rate of about 0 mL/hr to about 25 mL/hr, about 1 mL/hr to about 10 mL/hr, or about 3 mL/hr to about 7 mL/hr.

A voltage source 240 may apply an electric potential across the spinneret 220 and a target 250. In one example, the electric potential may be between about 10 kV and about 35 kV, between about 15 kV and about 40 kV, or between about 20 kV and about 25 kV. The electric potential 240 may aid the displacement system 226 in ejecting the solution 230 from the distal opening 225 of the orifice 224.

The solution may form a charged jet or stream 232 from the distal opening 225 to the target 250. The solution stream 232 may form a conical shape 233, called a Taylor cone, between the spinneret 220 and the target 250. As the solution stream 232 travels away from the opening 225, the cone 233 may begin to splay or stretch at a position 234 between the spinneret 220 and the target 250. In one example, the distance between the distal opening 225 and the target 250 may be between about 0.1 inches to about 6 inches, between about 0.5 inches to about 4 inches, or between about 1 inch to about 2 inches. Of course, other distances could be used depending on the device size and the target size. Position 234 need not be substantially intermediate the distal opening 225 and the target 250, and may be located at any desired distance between the distal opening and the target. The splaying or stretching action may create a plurality of fibers that may or may not dry upon reaching the target 250, depending on the volatility of the chosen solvent. The fibers may contact the target 250 to form a coating of nonwoven fibers thereon. The coating of nonwoven fibers may be configured as a network of fibers deposited on the target 250 to collectively form a sheet of nonwoven fibers.

In one example, an electrospinning apparatus similar to the electrospinning apparatus 200 may be used to prepare an occlusion device such as the occlusion device 100 described above. For example, an electrospinning apparatus may be used to apply a covering material to the support structure 110 to form the covering 111 as further described below.

Figure 3:
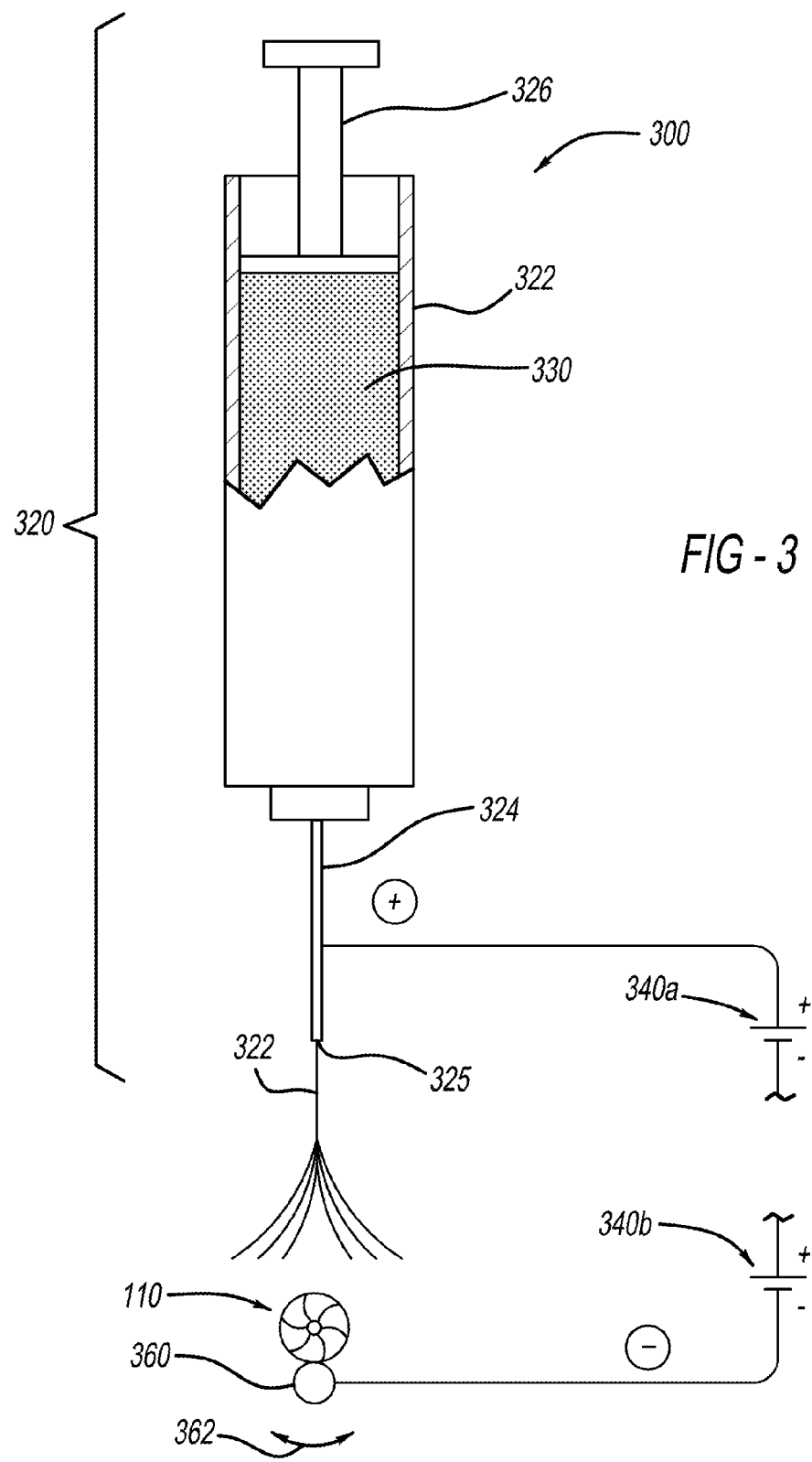
FIG. 3 illustrates an exemplary method step for electrospinning a solution onto an occlusion device support structure attached to a mandrel.

FIG. 3 illustrates one example of an electrospinning apparatus 300, which may be used to prepare the occlusion device 100 as further described below. For example, the electrospinning apparatus 300 may be used to electrospin a covering material (e.g., PET/UHMWPE solution) toward a rotating mandrel 360 to create an encapsulated supporting structure within a covering formed by the selected covering material. The electrospinning apparatus 300 may be similar to the electrospinning apparatus 200 described above. For example, the electrospinning apparatus 300 may include a spinneret 320 including a reservoir 322 that is fluidly coupled to an orifice 324. A solution 330 may be loaded into the reservoir 322 and driven by a displacement system 326 through a distal opening 325 of the orifice 324. An electric potential may be applied across the spinneret 320 and the mandrel 360. The solution may form a charged jet or stream 332 from the distal opening 325 to the mandrel 360. As the solution stream 332 travels away from the opening 325, the stream may begin to splay or stretch to create a plurality of fibers. The fibers may contact the mandrel 360 to form a coating of nonwoven fibers thereon.

The electrospinning apparatus 300 can coat components attached to the mandrel 360, such as the support structure 110 of the occlusion device 100. By attaching the support structure 110 to the mandrel 360, the coating applied by the apparatus 300 will form the covering 111 on the support structure 110 to create the occlusion device 100.

In one example, a voltage source may apply an electric potential across the spinneret 320 and the mandrel 360 as described above with reference to the voltage source 140. In another example, multiple voltage sources may be used to apply the electric potential. For example, a first voltage source 340a may be electrically coupled to the spinneret 320, and a second voltage source 340b may be electrically coupled to the mandrel 360 as shown in FIG. 3. The first voltage source 340a may generate an electric charge on the orifice 324. In other words, the first voltage source 340a may apply an electric potential between the orifice 324 and ground. Similarly, the second voltage source 340b may generate an electric charge on the mandrel 360. In other words, the second voltage source 340b may apply an electric potential between the mandrel 360 and ground.

The electric charge on the mandrel 360 may have an opposite sign relative to the electric charge on the orifice 324. In one example, the orifice 324 may be positively charged (i.e., the sign of the electric charge may be positive), and the mandrel 360 may be negatively charged (i.e., the sign of the electric charge may be negative). In another example, the orifice 324 may be negatively charged, and the mandrel 360 may be positively charged. This variable polarity can also apply to FIG. 2. The magnitude of the electric charge on the orifice 324 may be the same as or different than the magnitude of the electric charge on the mandrel 360. In one example, the magnitude of the electric charge on the orifice 324 relative to ground may be between about 5 kV and about 20 kV, preferably between about 6 kV and about 7.5 kV. Additionally, or alternatively, the magnitude of the electric charge on the mandrel 360 relative to ground may be between about 5 kV and about 20 kV, preferably between about 6 kV and about 7.5 kV. The orifice 324 and the mandrel 360 may have opposing charges such that the electric potential between the orifice and the mandrel may be between about 10 kV and about 40 kV, preferably between about 12 kV and about 15 kV.

In one example, the spinneret 320 may be configured as a 3 mL plastic syringe (e.g., a NORM-JECT® syringe commercially available from Air-Tite Products Co., Virginia Beach, Va.) equipped with a 23-Gauge disposable polymer-hub stainless steel needle. Additionally, or alternatively, the distance between the orifice 324 and the mandrel 360 may be between about 5 cm and about 25 cm, preferably between about 12 cm and about 15 cm. Additionally, or alternatively, the solution 330 may be extruded using a syringe pump at a substantially constant flow rate between about 0.5 mL/h and about 4 mL/h, preferably between about 0.5 mL/h and about 1.5 mL/h. Additionally, or alternatively, each of the first voltage source 340a and the second voltage source 340b may be configured as a high-voltage power supply capable of applying DC voltage up to about 20 kV.

FIG. 3 illustrates the mandrel 360 and the support structure 110 in a front view looking along the longitudinal axis of the mandrel 360. In one example, the mandrel 360 may have a substantially cylindrical or rod-like shape as shown in FIG. 3. In other examples, the mandrel 360 may have any other suitable shape sized and configured to allow attachment of the support structure 110. Preferably, the mandrel 360 may be sized and shaped for connection to a medical device (e.g., the support structure 110) as further described below.

The mandrel 360 and the spinneret 320 may be movable relative to one another. For example, the mandrel 360 may be moveable relative to the spinneret 320, or the spinneret 320 may be moveable relative to the mandrel 360, or both may be moveable. Such movement may enable the coating to applied to selected locations along the length of the device to the be coated, and will also allow for the coating to be applied in multiple passes. The mandrel 360 is rotatable about the longitudinal axis thereof. In other words, the mandrel 360 may be configured to rotate in a direction indicated by the arrow 362. In one example, the mandrel may be configured to rotate at a speed of between about 80 rpm and about 4000 rpm, or between about 100 rpm and about 500 rpm. The rotational speed of the mandrel 360 may be adjusted to adjust the diameter of the fibers produced during electrospinning. Increasing the rotational speed of the mandrel 360 may reduce the diameter of the fibers. Decreasing the rotational speed of the mandrel 360 may increase the diameter of the fibers.

The mandrel 360 may be movable in a direction substantially parallel to the longitudinal axis thereof. In other words, the mandrel 360 may be configured to translate (e.g., in a forward or backward longitudinal direction) relative to the spinneret 320. Additionally, or alternatively, the mandrel 360 may be movable in a direction transverse to the longitudinal axis of the mandrel. In other words, the mandrel 360 may be configured to translate (e.g., in an up, down, or sideways transverse direction) relative to the spinneret 320. Such rotation and/or translation (e.g., longitudinal or transverse translation) of the mandrel 360 relative to the spinneret 320 may enable coating of the outer surface of the mandrel or device attached thereto, or a portion thereof, with electrospun fibers as further described below. Such a coating may be achieved by any relative motion between the mandrel 360 and the spinneret 320. For example, movement of the mandrel 360 relative to the spinneret 320 may be achieved by maintaining the spinneret in a constant position while moving the mandrel, by maintaining the mandrel in a constant position while moving the spinneret, and/or by moving the mandrel and the spinneret relative to one another. In one example, the mandrel may rotate and the spinneret may translate in a longitudinal direction relative to the mandrel.

The relative movement of the mandrel 360 with respect to the spinneret 320 may influence several properties of the resulting coating of fibers. For example, increasing the speed of the relative motion may cause a reduction in the thickness of the coating. This may be caused, for example, because a portion of the mandrel 360 may be disposed in the path of the stream 332 for a shorter period of time at increased speeds. Additionally, or alternatively, increasing the speed of the relative motion may cause the fibers to be increasingly aligned with one another. This may affect the strength, resiliency, and/or porosity of the coating. Also for example, as the distance between the spinneret 320 and the mandrel 360 is increased, the solution stream 332 may be required to travel a greater distance before reaching the mandrel. This may affect the splaying and/or drying characteristics of the solution stream 332, which may affect the properties of the resultant coating.

In any of the examples described herein, the mandrel 360 may be formed from any suitable conductive material known in the art. For example, the mandrel 360 may be formed from a metallic material such as stainless steel (e.g., electropolished stainless steel) or chrome. In another example, the mandrel 360 may be formed from a non-metallic material such as a conductive plastic material. The mandrel 360 may include a release layer disposed on the outer surface thereof to aid in removing the prosthesis 100 from the mandrel as further described below. The release layer may be formed from any material known in the art. Preferably, the release layer may be formed from a non-stick material such as, for example, PTFE, sodium bicarbonate, a silicone lubricant, or any other biocompatible lubricant.

Figure 4:
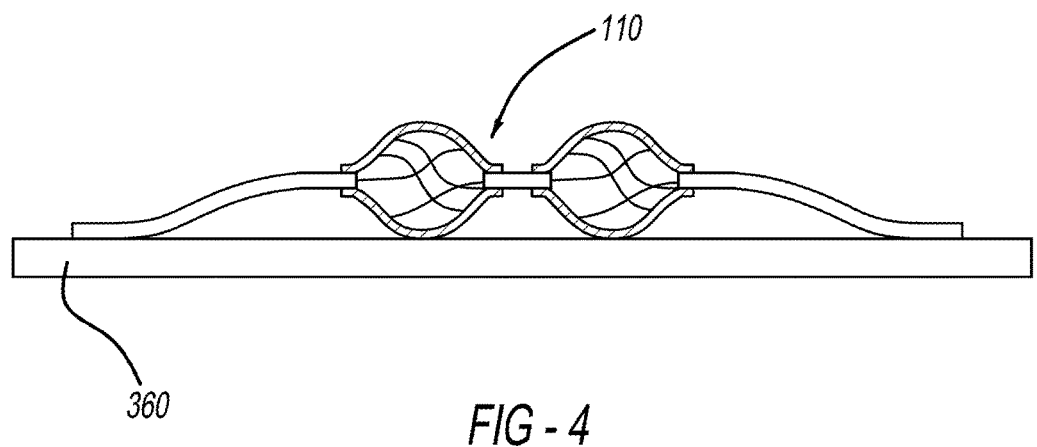
FIG. 4 is a side view of the support structure attached to the mandrel.

The support structure 110 may be placed on the mandrel 360 as shown in FIG. 4. As described above, the support structure 110 may have a relaxed nominal diameter so that the device 100 will radially expand upon being deployed after being radially compressed and lengthened for delivery. The support structure 110 is preferably attached to the mandrel 360 while the structure 110 is in a radially reduced and longitudinally lengthened state. However, the support structure 110 does not necessarily need to be fully extended or lengthened to its delivery configuration. Rather, the support structure is preferably in an intermediate state between the nominal state and the lengthened state, such that the structure 110 defines a generally bulbous shape. This can be done to diminish or eliminate migration of the device, because during the coating process the covering forces can apply an external force inwardly. This attachment to the mandrel in such a bulbous shape can also allow for a preferred shape for the coating process. However, it will be appreciated that the support structure 110 can be attached to the mandrel 360 in a further lengthened state, or its nominal state, to apply the coating 111 thereto in other approaches.

The support structure 110 can be attached to the mandrel 360 in a manner known in the art. For example, it can be attached via an adhesive, a mechanical connection, bonding, clamping, threading, or the like. Preferably, the support structure 110 is attached to the mandrel 360 in a releasable manner such that the support structure can be easily removed from the mandrel 360 after the coating process is complete. For example, the support structure 110 can be releasably clamped to the mandrel 360.

A layer of nonwoven fibers may be formed on the support structure 110 by electrospinning the solution 330 from the orifice 324 onto the support structure 110. FIG. 3 illustrates the electrospinning apparatus 300 described above configured to form a layer of nonwoven fibers on the support structure 110. The support structure 110 may be positioned between the spinneret 320 and the mandrel 360. The solution 330 may be discharged from the spinneret 320 toward the mandrel 360 as described above. The stream 322 may contact the support structure 110 to form the layer of nonwoven electrospun fibers thereon.

In one example, the mandrel 360 may be moved rotationally about the longitudinal axis thereof, which may cause corresponding rotation of the support structure 110. The solution 330 may be discharged from the orifice 324 and attracted to the mandrel 360 by the electrical potential applied between the orifice and the mandrel as described above. The rotation of the support structure 110 may cause the resultant coating of nonwoven fibers to be distributed about the circumference of the support structure 110. Additionally, some gravitational force and centrifugal forces can provide additional covering collection onto the structure 110. Additionally, or alternatively, the spinneret 320 may be translated longitudinally relative to the support structure 110 while discharging the solution 330 from the orifice 324. The translation of the spinneret 320 may cause the resultant coating of nonwoven fibers to be distributed about the length of the support structure 110. In one example, the support structure 110 may be rotated and the spinneret 320 may be translated to form a layer of nonwoven fibers covering substantially the entire circumference of the support structure 110 along at least a portion of the length of the support structure 110. Preferably, the support structure 110 is fully coated along both its circumference and its length. During the coating process, the support structure 110 can be adjusted on the mandrel 360 if necessary to provide the desired coverage.

The above described longitudinally movement of the mandrel 360 and the attached support structure 110 relative to the spinneret 320 may be referred to as a "pass." A single pass occurs when the spinneret 320 moves in one direction relative to mandrel (caused by either or both of the mandrel 360 and spinneret 320 translating). The non-woven fibers that make up the coating 111 once fully applied can be applied to the support structure over multiple passes. For example, the support structure 110 can be coated by way of 5-7 passes in total, in one approach. The passes can be performed in multiple stages. For example, 2-3 passes can be applied in a first state, and 3-4 passes can be applied in a second state. Splitting up the passes can allow for the addition of additives (sprays) and/or soaking, and additional fibers can thereby be added at a later point. Of course, the number of passes and/or stages can vary depending on the needs of the user and the desired thickness and coverage.

In one approach, the two-stage approach described above totaling between 5-7 passes can result in a preferred thickness of the coating 111 of between 60 μm and 120 μm. It will be appreciated that additional passes would result in additional thickness, and reduced passes would result in a thinner coating 111. Furthermore, as described above, the rotational speed of the mandrel 360 relative to the relative translational movement of the spinneret 320 to the mandrel 360 can also vary the thickness of the coating 111. Accordingly, it will be appreciated that myriad modifications to the relative translation and rotational speeds, as well as the number of passes, can be made to create different coating distribution on the support structure 110.

The above process has described an electrically charged mandrel. Additionally, or alternatively, in one example, the support structure 110 may be electrically charged during electrospinning of the layer of nonwoven fibers on the surface thereof. In other words, an electrical potential may be applied between the orifice 324 and the support structure 110. The electrical potential may aid in attracting the solution 330 discharged from the orifice 324 as described above. The electrical charge on the support structure 110 may be generated, for example, by the electrical charge on the mandrel 360 and the proximity or attachment of the support structure 110 to the mandrel 360. Additionally, or alternatively, the support structure 110 may be electrically coupled to the mandrel 360 (e.g., with a conductive wire or by contact with the mandrel). The electrical charge on the support structure 110 and/or the mandrel 360 may vary during electrospinning. For example, the electrical charge may be reduced by an insulating effect of the layers of electrospun fibers formed on the mandrel 360 and/or the support structure 110 that occurs during the process. The electrical charges of the mandrel 360, the support structure 110, and/or the spinneret 320 may be adjusted (e.g., increased) during electrospinning to compensate for such an insulating effect.

The support structure 110 and the covering 112 collectively form the occlusion device 100 upon conclusion of the coating process.

The occlusion device 100 (e.g., the support structure 110 with the covering 112 of electrospun fibers attached thereto) may be removed from the mandrel 360. To that end, the mandrel 360 may include a release layer applied to the outer surface thereof. The release layer may reduce the attractive force (e.g., adhesive force) or the frictional force between the electrospun fibers disposed on the support structure 110 and the outer surface of the mandrel 360 to aid in removing the prosthesis 100 from the mandrel in an undamaged condition. Upon removal from the mandrel 360, the support structure 110 may longitudinally contract and radially expand to its relaxed nominal shape. Forming the electrospun fibers on the support structure 110 in the intermediate lengthened state may enhance the flexibility of the prosthesis 100. For example, upon longitudinal contraction of the support structure 110 to the nominal shape, the tension of the coating 111 of electrospun fibers may be reduced, which may enable increased movement or flexibility of the covering. Additional flexibility and resistance to strain is afforded by the composition of the material in the solution 330.

An excess length of the covering 112 formed by the electrospun fibers may extend beyond at least one of the proximal or the distal ends segment of the support structure 110. At least a portion of the excess length of the covering may be removed from the device 100. Alternatively, the excess covering material 112 can be tied down using PET fibers to fix the covering 112 to the support structure 110 and for flap avoidance.

Additionally, or alternatively, the fully or partially encapsulated electrospun covered support structure (e.g., the covered occlusion device 110) may be post-processed using manufacturing techniques (e.g., laser welding/marking, mechanical punching, trimming and suturing, etc.) to create varying porosity if desired.

As described above, the electrospinning apparatus will apply a solution 330 to the support structure 110 to create the covering 111 thereon. Thus, the material properties of the covering 111 depend on the solution 330.

Figure 5:
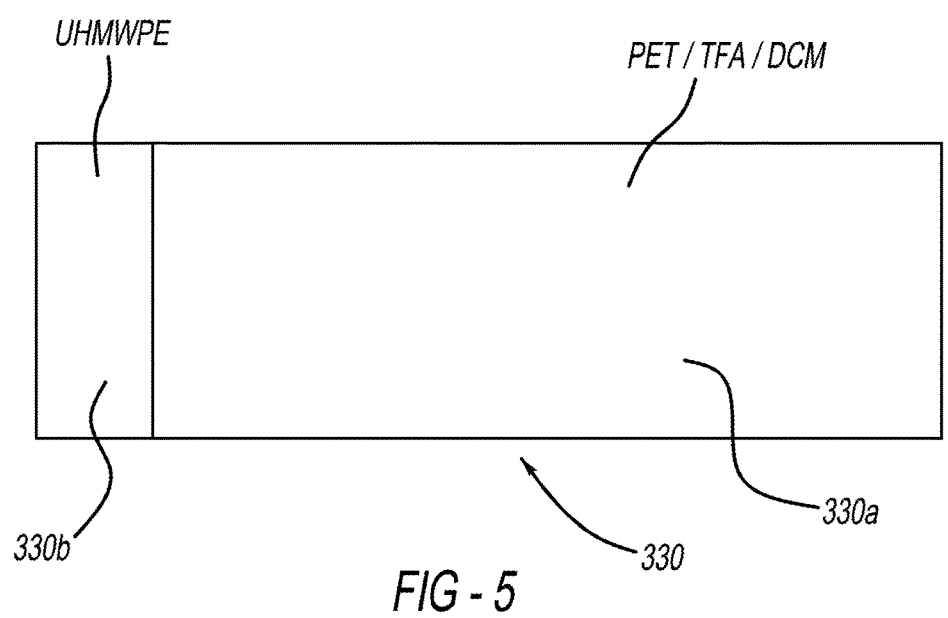
FIG. 5 is a schematic representation of the component parts that are ultimately dispersed within a covering mixture applied to the support structure.

With reference to FIG. 5, in a preferred form, the solution 330 includes a combination of PET and UHMWPE, and this solution is process and applied to form the covering 111 on the support structure 110. Therefore, the covering includes a combination of electrospun PET (ePET) and UHMWPE microparticles in an electrospun nonwoven fiber configuration created by the electrospinning apparatus 200 or 300.

The solution 330 is, more particularly, a combination of a solution portion 330a and a suspension portion 330b. The solution portion 330a can include a polymer solution of PET in approximately 50:50 trifluoroacetic acid (TFA) and dichloromethane (DCM or methylene chloride) at a predetermined concentration, typically between about 0.10 g/mL and about 0.17 g/mL. The solution portion 330a can be approximately 15% PET and 85% 50:50 TFA/CDM.

The suspension portion 330b is in the form of UHMWPE microparticles that are suspended in the overall solution 330. FIG. 5 illustrates a schematic representation of the components of the suspension portion 330b and the solution portion 330a, but it will be appreciated that the microparticles are ultimately dispersed throughout the solution 330. These microparticles are not dissolved in the solution portion 330a and remain as suspended solids. The microparticles are preferably approximately 30 microns. However, other sizes of microparticles can also be used, such as in the range of 20-40 microns.

The suspension portion 330b of UHMWPE is preferably approximately 5% of the solution 330, with 95% of the solution 330 being the solution portion 330a of PET and 50:50 TFA/DCM. This particular mixture has been found to provide increased resistance to strain relative to 100% PET/TFA/DCM solution without UHMWPE microparticles suspended therein. For example, the solution 330 described above having the UHMWPE microparticles has been found to permit the support structure 110 to be pulled approximately twice the distance (100% increase in allowed pulled length) longitudinally relative to 100% PET solution.

However, other amounts of UHMWPE can also be added to the PET solution portion 330a. For example, a solution 330 having 10% UHMWPE microparticles and 90% PET solution has been found to allow for 75%-80% increased pulling distance. The amount of UHMWPE increased, but the increased pulling distance was shorter than the 5% UHMWPE.

Other amounts of UHMWPE were also tested. A solution 330 with 1% UHMWPE resulted in little increased pulling distance. A solution with 15% UHMWPE would not be properly electrospun.

Additionally, or alternatively, the covering material may be electrospun simultaneously with additives or pharmacological agents such as, for example, lauric acid, levulinic acid, or polyethylene glycol (e.g., having a molecular weight of about 300, about 600, or any other suitable molecular weight). Electrospinning the covering material with other materials may affect the mechanical properties (e.g., flexibility or strength) of the graft or covering material. Additionally, or alternatively, electrospinning the graft or covering material with other materials may affect the frictional properties and/or enable a reduced profile of the graft or covering material.

A covering formed by electrospinning as described herein may include a plurality of nonwoven fibers. In other words, the electrospun fibers may be configured as a mesh of fibers as opposed to a patterned weave or knit of fibers. The electrospun fibers may be nanofibers having a diameter of less than about 1,000 nm. The electrospun covering 111 may substantially conform to the underlying support structure 110. In other words, the electrospun covering 111 may substantially take the shape of the support structure 110 and may be substantially free of ridges or puckering which may be caused by mechanical attachment mechanisms (e.g., sutures). Additionally, or alternatively, the electrospun covering 111 may be substantially seamless. In other words, the covering 111 may be substantially free of seams which may be formed, for example, by stitching together or otherwise attaching adjacent edges of one or more sheets of covering material.

Applying a covering material to a support structure by electrospinning as described herein enables formation of an occlusion device having a reduced profile. For example, the covering 111 may be attached to the support structure without the use of any attachment material (e.g., suture, tape, such as PTFE-FEP bonding tape, glue, or lamination material) or additional processing steps (e.g., mechanical attachment, pressure bonding, chemical treatment, or thermal bonding). In other words, the prosthesis may be substantially free of an extrinsic attachment mechanism. Such attachment material may increase the thickness of the coating resulting in a prosthesis having a larger profile.

An occlusion device with a reduced thickness may enable an occlusion device having a reduced profile. Such a low-profile occlusion device may be delivered using a sheath having a reduced profile relative to conventional introducer sheaths. This may aid in advancing the sheath within a body vessel to the delivery site within the patient's anatomy.

The low profile of the device due to the thickness of the covering 111 in addition to the increased resistance to the strain and ability to extend longitudinally and compress radially during delivery adds to the device's ability to be delivered via a low profile delivery sheath.

Direct encapsulation of the support structure may reduce abrasive forces between the covering 111 and the support structure 110. For example, the portion of the support structure 110 encapsulated within the covering may be substantially unable to move relative to the covering, thereby reducing abrasion between the encapsulated support structure and the graft material. Additionally, or alternatively, direct encapsulation of the support structure 110 may enable formation of a substantially non-porous covering that is substantially free of suture holes or other openings formed therein. This substantially non-porous covering can be beneficial for quickly occluding a body vessel.

While the preferred solution for the occlusion device 110 was described above, other solutions for use in the electrospinning process of the present disclosure may include any suitable liquids containing materials to be electrospun. For example, solutions may include, but are not limited to, suspensions, emulsions, melts, and hydrated gels containing the materials, substances, or compounds to be electrospun. Solutions also may include solvents or other liquids or carrier molecules. Solutions may include, for example, any of the materials described in U.S. Pat. No. 7,799,261 to Orr et al., which is incorporated herein by reference. In one example, the solution 330 may include a PET such as, for example a DACRON® leg-fabric commercially available from Invista, Wichita, Kans. The solution 330 may include a polymer solution of PET in approximately 50:50 trifluoroacetic acid (TFA) and dichloromethane (DCM or methylene chloride) at a predetermined concentration, typically between about 0.10 g/mL and about 0.17 g/mL solvent. Such a solution is similar to the preferred solution described above, but without the UHMWPE microparticles. Such a solution would not result in the increased strain capabilities of the preferred solution.

Additionally, or alternatively, solutions may include one or more bioactive agents. A therapeutically effective amount of a bioactive agent may be incorporated into the covering 111 produced by the electrospinning process for implantation within a patient. The bioactive agent may be selected to perform a desired function upon implantation. For example, the bioactive agent may be selected to treat indications such as atherosclerosis, renal dialysis fistulae stenosis, or vascular graft stenosis. A covering material 111 including a bioactive agent may be useful when performing procedures such as coronary artery angioplasty, renal artery angioplasty, or carotid artery surgery. Also for example, a bioactive agent such as a growth factor may be selected to promote ingrowth of tissue from the interior wall of a body vessel. An anti-angiogenic or antineoplastic bioactive agent such as paclitaxel, sirolimus, or a rapamycin analog, or a metalloproteinase inhibitor such as batimastaat may be included to mitigate or prevent undesired conditions in the vessel wall, such as restenosis. Sclerosing agents can help facilitate vessel clamp and occlusion. Many other types of bioactive agents also may be included in the solution.

Although the electrospinning process has been described in relation to applying a covering to a support structure, this disclosure is not so limited. The electrospinning process described above may be used to apply any type of coating to any type of medical device. For example, the electrospinning process may be used to apply a coating of a therapeutic agent to a stent or a covered stent (e.g., a stent graft).

The electrospinning process described above to apply the coating 111 to the support structure 110 to create the occlusion device 100 can also include additional steps.

In one approach, the support structure 110 can be soaked in a sol-gel to improve covering adhesion. In this approach, the support structure can be soaked in a $SiO_2$ sol-gel for approximately 1 hour at approximately 40 degrees C. Following this soaking process, the support structure can then be dried in air for approximately 1 hour at approximately 60 degrees C. This step is not required, but can provide for improved covering adhesion to the metallic surface of the support structure 110, if desired.

Following the optional sol-gel soaking, the support structure 110 can be fixed onto the mandrel 360 as described above. More specifically, the structure 110 can be lengthened from its nominal state and fixed to the mandrel 360 in this shape.

The above described electrospinning process can be performed to coat the support structure 110 with the coating 111. More particularly, the first stage of electrospinning can be performed, where 2-3 passes of the PET/UHMWPE solution are applied, preferably resulting in a thickness of approximately 30-60 μm.

Following the application of the coating 111 of the first stage of passes, the device 100 can have a further sol-gel applied. In this approach, a $TiO_2/SiO_2$ sol-gel of varying ratios can be applying to the device 100. In one approach, the $TiO_2/SiO_2$ ratio is about 9:1. In a preferred form, about 0.15-0.30 mL of sol-gel is applied in this step. The sol-gel can be applying in a manner known in the art, such as by spraying, dipping, or the like. The application of this sol-gel to the device 100 can help to limit, reduce, or eliminate delamination of the coating 111.

Following the first stage of electrospinning passes, the second stage of passes is performed, where preferably 3-4 passes of the PET/UHMWPE solution are applied via electrospinning, resulting in a preferred thickness of about 30-60 μm and a total thickness of about 60-120 μm.

The above described $TiO_2/SiO_2$ sol-gel application can be performed after the second stage instead of after the first stage. Alternatively, this sol-gel application can be performed after both stages.

Following the above, the device 100 and the attached mandrel 360 can be soaked in ethanol and placed in a water bath.

Following this ethanol soaking and water bath, the device 100 can be removed from the mandrel 360.

As described above, there may be excess covering 111 extending beyond the proximal and distal ends of the device 100. This excess covering can be tied down using PET fibers for covering fixation and flap avoidance.

The device 100 having the support structure 110 covered by the covering 111 can then be placed in a drying oven at approximately 60 degrees C. for approximately 15 minutes.

The support structure 110 can also be removed and reoriented on the mandrel 360 during the above process depending on the needs of the user.

The above described process results in device 100 with a covering 111 that can conform to a complex support structure 110 to thereby define a complex vascular plug or occlusion device. This covered device 100 is capable of undergoing increased longitudinal and radial elongation of the support structure 110 while maintaining the integrity of the covering 111, relative to a support structure with only PET and no UHMWPE microparticles. This increased ability to strain the device 100 allows for an increased radial expansion while being able to be longitudinally lengthened and radially reduced for insertion into a low-profile delivery sheath for delivery to a target vessel within the body. For example, the device 100 can be loaded into a delivery sheath of as little as 3 or 4 French. This reduced delivery capability can allow for delivery to smaller visceral vessels as well as larger vessels.

The above described process can be applied to other medical devices, as well, and is not limited to wire constructed support frames. For example, the above process could be used for various stent grafts or other PET graft/covered medical devices for the treatment of vascular and non-vascular disease.

Furthermore, upon delivery of the device 100 and release from the delivery sheath, the device 100 will return to its nominal shape and span the target vessel almost immediately. Occlusion can be achieved without relying on delayed embolization. The device 100 also does not suffer from the coil migration problems associated with other types of coil-based occlusion devices.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A medical device for placement within a body vessel for providing vessel occlusion, the device comprising:
   a support structure having proximal and distal ends and defining a longitudinal axis therebetween, wherein the support structure is biased toward a nominal state having a radial expanded and longitudinally shortened configuration and extendable from the nominal position to a lengthened state having a radially reduced and longitudinally lengthened configuration;
   at least one layer of nonwoven electrospun fibers attached to and encapsulating the support structure; and
   wherein the electrospun fibers comprise a mixture of Polyethylene Terephthalate (PET) composition and Ultra High Molecular Weight Polyethylene (UHMWPE) micro-particles.

2. The medical device of claim 1, wherein the mixture comprises approximately 5% UHMWPE microparticles and 95% PET composition.

3. The medical device of claim 2, wherein the PET composition includes approximately 15% PET solids and 85% 50:50 trifluoroacetic acid and dichloromethane.

4. The medical device of claim 1, wherein the microparticles are approximately 30 micron micro-particles.

5. The medical device of claim 1, wherein the at least one layer comprises a first layer and a second layer.

6. The medical device of claim 5, wherein the first layer has a thickness of about 30-60 microns and the second layer has a thickness of about 30-60 microns.

7. The medical device of claim 5 further comprising a coating of $TiO_2/SiO_2$ sol-gel applied to at least one of the first and second layers.

8. The medical device of claim 7, wherein the coating is disposed between the first and second layers.

9. The medical device of claim 7, wherein the coating has a ratio of approximately 9:1 $TiO_2:SiO_2$.

10. The medical device of claim 7, wherein the coating is disposed on an outermost surface of the device.

11. The medical device of claim 1, wherein the support structure comprises a first mesh and a second mesh, and an intermediate portion disposed therebetween, wherein the intermediate portion has a smaller diameter than the proximal and distal portions in both the nominal and lengthened states, wherein each of the first mesh and second mesh comprise a plurality of wires.

12. The medical device of claim 1 further comprising PET fibers tied around the electrospun fibers at both the proximal and distal ends.

13. The medical device of claim 1, wherein the support structure and attached covering can withstand approximately double the strain of the support structure with an alternative covering of electrospun fibers having no UHMWPE.

14. A method for coating a support structure with a non-woven electrospun material, the method comprising:
   attaching a support structure to a conductive mandrel;
   rotating the mandrel;
   applying a mixture of ultra high molecular weight polyethylene (UHMWPE) microparticles and Polyethylene Terephthalate (PET) solution to the support structure by electrospinning; and
   coating the support structure with non-woven electrospun fibers produced by electrospinning the mixture to produce at least one layer of non-woven electrospun fibers, the at least one layer of nonwoven electrospun fibers attached to and encapsulating the support structure;
   wherein the support structure includes proximal and distal ends and defines a longitudinal axis therebetween, wherein the support structure is biased toward a nominal state having a radial expanded and longitudinally shortened configuration and extendable from the nominal position to a lengthened state having a radially reduced and longitudinally lengthened configuration.

15. The method of claim 14, wherein the at least one layer comprises a first layer and second layer, and the first layer and second layer are provided in a first coating step and a second coating step.

16. The method of claim 15, further comprising applying a $TiO_2/SiO_2$ solution to at least one of the first layer and the second layer, wherein the applying step is performed between the first and second coating steps.

17. The method of claim 15, further comprising applying a $TiO_2/SiO_2$ solution to at least one of the first layer and the second layer, wherein the applying step is performed after the first and second coating steps.

18. The method of claim 15, wherein the first coating step includes translating the support structure relative to the mandrel over 2-3 passes and the second coating step includes translating the support structure relative to the mandrel over 3-4 passes.

19. The method of claim 14, further comprising tying PET fibers around proximal and distal ends of the at least one layer.

20. The method of claim 14, wherein the mixture includes about 4%-10% UHMWPE microparticles in suspension and the remainder comprises the PET solution.

* * * * *